United States Patent
Hayashi et al.

[11] Patent Number: 5,856,320
[45] Date of Patent: Jan. 5, 1999

[54] CEPHEM COMPOUNDS, THEIR PREPARATION AND THEIR USE AS ANTIMICROBIAL AGENTS

[75] Inventors: Sadao Hayashi; Yasuyuki Kurita, both of Osaka-fu, Japan

[73] Assignee: Katayama Seiyakusyo Co., Ltd., Osaka, Japan

[21] Appl. No.: 732,856

[22] Filed: Oct. 15, 1996

[30] Foreign Application Priority Data

Oct. 17, 1995 [JP] Japan ................................. 7-268358

[51] Int. Cl.⁶ ........................ C07D 501/56; A61K 31/53
[52] U.S. Cl. ........................................ 514/202; 540/222
[58] Field of Search ............................ 540/222; 514/202

[56] References Cited

U.S. PATENT DOCUMENTS

| | | | |
|---|---|---|---|
| 4,191,762 | 3/1980 | Kamiya et al. | 544/22 X |
| 4,225,707 | 9/1980 | Kamiya et al. | 544/16 |

FOREIGN PATENT DOCUMENTS

| | | |
|---|---|---|
| 203271 | 12/1986 | European Pat. Off. . |
| 304858 | 3/1989 | European Pat. Off. . |
| 332156 | 9/1989 | European Pat. Off. . |
| 517041 | 12/1992 | European Pat. Off. . |
| 2728766 | 1/1978 | Germany . |
| 2028170 | 1/1990 | Japan . |

OTHER PUBLICATIONS

Hara, R., et al, The Journal of Antibiotics, 49(11), 1162–1171, 1179–1181, and 1182–1185 (1996).

35th Interscience Conference on Antimicrobial Agents and Chemotherapy, San Francisco, Tamura, A., et al, Abstract #2270 (1995).

Hayashi, S., et al, Chemical Abstracts, 119, 270910h (1993).

Hayashi, S., Chemical Abstracts, 122, 187263r (1995).

Hayashi, S., et al, Chemical Abstracts 122, 265170z (1995).

Hayashi, S., et al, Chemical Abstracts, 122, 290585w (1995).

35th Interscience Conference on Antimicrobial Agents and Chemotherapy, San Francisco, Tamura, A., et al, Abstract #2271 (1995).

35th Interscience Conference on Antimicrobial Agents and Chemotherapy, San Francisco, Atsumi, K., et al, Abstract #2272 (1995).

Cram and Hammond, "Organic Chemistry" 2nd Ed. (1964) McGraw Hill Book Co, New York, pp. 565–567.

*Primary Examiner*—John M. Ford

[57] ABSTRACT

Novel cephalosporin derivatives of formula (II):

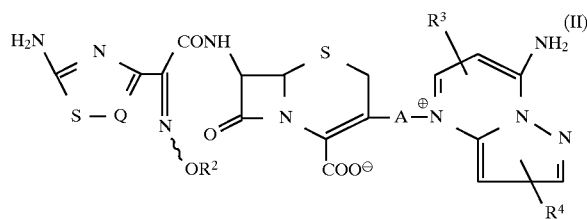

wherein $R^2$ is hydrogen, methyl, or fluoromethyl; $R^3$ is hydrogen, methyl or carboxyl; $R^4$ is hydrogen or methyl; A is methylene or propenylene; Q is nitrogen or CH, and pharmaceutically acceptable salts, solvates, hydrates and esters thereof, a process for their preparation and an antimicrobial composition containing them.

6 Claims, No Drawings

1
CEPHEM COMPOUNDS, THEIR PREPARATION AND THEIR USE AS ANTIMICROBIAL AGENTS

BACKGROUND OF THE INVENTION

1. Field of the Invention

The present invention relates to novel cephem compounds, their preparation and their use as antimicrobial agents, particularly, against Methicillin-Resistant Staphylococcus aureus (MRSA) and antimultipledrug-resistant bacteria.

2. Background Information

A variety of cephem compounds having both an aromatic or aliphatic quaternary ammonium methyl or propenyl group at the 3-position of a cephem skeleton and [2-(2-aminothiazol-4-yl)- or 2-(5-amino-1,2,4-thiadiazol-3-yl)]-2-hydroxy (or substituted hydroxy) iminoacetamido group at the 7-position have so far been developed and many patent applications concerning those compounds, for instance, Japanese Patent Publication A (TOKKAISHO) Nos. 55-149289 (1980), 57-56485 (1982), 57-192394 (1982), 58-159498 (1983), 60-224694 (1985), 60-237090 (1985), 61-7280 (1986), 62-149682 (1987), 62-270589 (1987), and (TOKKAIHEI) Nos. 2-28170 (1990), 4-26692 (1992) and 7-41484 (1995) have been filed. However, the compounds of the present invention having substituted (or unsubstituted) 7-aminopyrazolo-[1,5-a]pyrimidinium ring in a substituent at the 3-position of the cephem skeleton have not been disclosed.

Many Cephalosporin derivatives have been developed and cephem-type antibiotics have been widely used for the treatment of diseases of human beings and animals caused by pathogenic bacteria. However, the antimicrobial activities of those compounds are not sufficiently satisfactory. There is still a need therefore for compounds having excellent and broad antimicrobial activities against both gram-positive and gram-negative bacteria, for instance, against MRSA and against Pseudomonas aeruginosa.

As a result of extensive study on cephalosporin derivatives having a satisfactory antimicrobial activity against Gram-positive bacteria and also having strong antimicrobial activity against Gram negative bacteria, now it has been found that cephalosporin derivatives having 7-aminopyrazolo[1,5-a]pyrimidine as substituents at the 3-position of the cephem skeleton have a wide antimicrobial spectrum against both Gram-positive bacteria and Gram-negative bacteria including MRSA and Pseudomonas aeruginosa.

SUMMARY OF THE INVENTION

An object of the present invention is to provide novel cephalosporin derivatives and salts, hydrates and salts of hydrates thereof, a process for producing the same and a pharmaceutical composition for use in the prevention and/or treatment of infectious diseases which comprises the novel cephalosporin derivatives as active components.

In the first aspect, the invention provides a compound of formula (I):

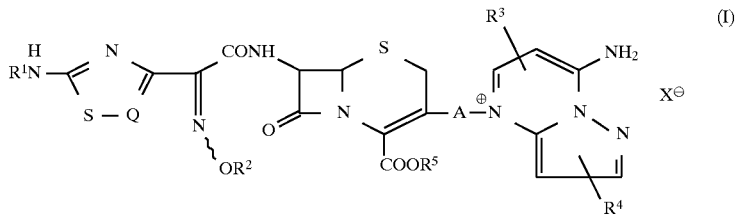

wherein $R^1$ is hydrogen or an amino protecting group; $R^2$ is hydrogen, a lower alkyl or fluoromethyl; $R^3$ is hydrogen, a lower alkyl, carboxyl or a protected carboxyl group; $R^4$ is hydrogen or a lower alkyl; $R^5$ is hydrogen, an anion or a carboxyl-protecting group; A is methylene or propenylene; X is an organic or inorganic anion, provided that X is excluded when $R^5$ is an anion; Q is nitrogen or CH, and the wavy line represents a bond of anti-form or syn-form, or a pharmaceutically acceptable salt thereof.

In the second aspect, the invention provides an antimicrobial composition which comprises as an active ingredient at least one of the compounds of formula (II):

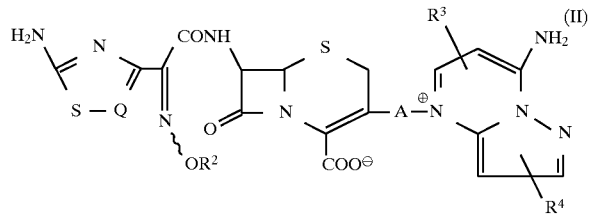

wherein $R^2$ is hydrogen, methyl or fluoromethyl; $R^3$ is hydrogen, methyl or carboxyl; $R^4$ is hydrogen or methyl; A is methylene or propenylene; Q is nitrogen or CH, and the wavy line represents a bond of anti-form or syn-form, or a pharmaceutically acceptable salt thereof, and together with an inert carrier or diluent.

In the third aspect the invention provides a process for producing a compound of formula (III):

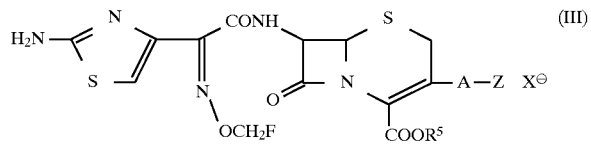

wherein $R^5$ is hydrogen, an anion or a carboxyl-protecting group; A is methylene or propenylene; X is an organic or inorganic anion, provided that X is excluded when $R^5$ is an anion, and Z is a halogen or a compound of formula (IV):

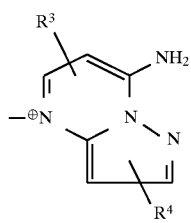

wherein $R^3$ is hydrogen, a lower alkyl, carboxyl or a protected carboxyl group; and $R^4$ is hydrogen or a lower alkyl, which comprises reacting the compound of formula (V):

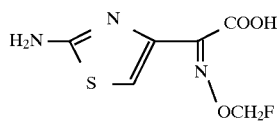

with a compound of formula (VI):

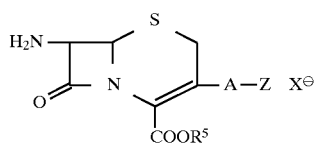

wherein $R^5$, A, X, and Z have the same meanings as above (referred to as Preparation C below).

In the fourth aspect, the invention provides the compound of formula (V):

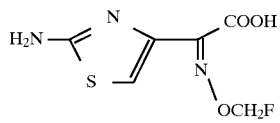

which is a novel compound and an intermediate for producing of the compounds of formula (I).

DETAILED DESCRIPTION OF THE INVENTION

Among the compounds of formula (I), preferred are the cephalosporin derivatives are preferred wherein $R^1$ is hydrogen; $R^2$ is hydrogen, methyl or fluoromethyl; $R^3$ is hydrogen, methyl or carboxyl; $R^4$ is hydrogen or methyl, and the wavy line represents a bond of syn-form. Particularly preferred are 7β-[2-(5-aminothiadiazol-3-yl)-2-syn-fluoro-methoxyiminoacetamido]-3-(7-aminopyrazolo[1,5-a]pyrimidinium-4-yl)methyl-3-cephem-4-carboxylate, 7β-[2-(2-amino-thiazol-4-yl)-2-fluoro-syn-methoxyiminoacetamido]-3-(7-amino-pyrazolo[1,5-a]pyrimidinium-4-yl)methyl-3-cephem-4-carboxylate, 7β-[2-(2-aminothiazol-4-yl)-2-synmethoxy-iminoacetamido]-3-(7-aminopyrazolo[1,5-a]pyrimidinium-4-yl)methyl-3-cephem-4-carboxylate and the compound of formula (V):

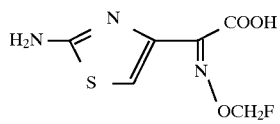

In the specification the term "a lower alkyl" covers an alkyl group having between 1 and 5 carbon atoms, for example, methyl, ethyl, propyl and iso-propyl, preferably methyl and ethyl, more preferably methyl.

As typical examples of pharmaceutically acceptable salts of the present invention, for example, an inorganic basic salt such as sodium, potassium, calcium, magnesium and aluminium; an organic salt such as ethanol amine, N,N'-dibenzylethylenediamine and procaine; an inorganic acid addition salt such as hydrochloric acid, hydrobromic acid, nitric acid, sulfuric acid, phosphoric acid and perchloric acid; an organic acid addition salt such as acetic acid, lactic acid, propionic acid, maleic acid, fumaric acid, tartaric acid, malic acid and citric acid; an amino acid salt such as glutamic acid, aspartic acid, lysine, arginine and ornithine; a sulfonic acid addition salt such as methane-sulfonic acid and p-toluene-sulfonic acid can be mentioned.

Examples of pharmaceutically acceptable esters of the invention include acetoxymethyl and pivaloyloxymethyl as alkanoyloxyalkyl groups; glycyloxymethyl and ethoxy-carbonyloxyethyl as alkoxycarbonyloxyalkyl groups; indanyl, phthalidyl and 5-methyl-2-oxo-1,3-dioxolen-4-yl-methyl and other ester known and used in the penicillin and cephalosporin arts. Such esters are prepared by conventional techniques known in the art.

Within the scope of the invention, are also included such compounds that retain the same physiological or pharmacological effectiveness as the free compounds of the present invention in the living body, for example, derivatives, hydrates, and addition salts thereof.

Production of the compound of the present invention is described below. The compound of the general formula (I) can be produced by either of two reaction schemes as shown in Preparation A and Preparation B as follows.

The compound of formula (I) wherein $R^2$ is $CH_2F$ can be also prepared by the process as shown in Preparation C mentioned above.

Preparation A

A compound of formula VII:

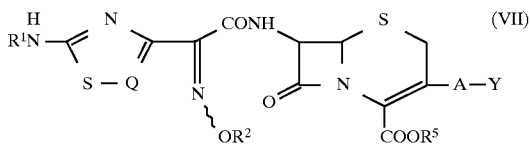

wherein $R^1$ is hydrogen or an amino protecting group, $R^2$ is hydrogen, a lower alkyl or fluoromethyl, $R^5$ is hydrogen or a carboxyl-protecting group, A is methylene or propenylene, Q is nitrogen or CH, Y is a leaving group and the wavy line represents a bond of anti-form or syn-form, is reacted with either a compound of formula (VIII):

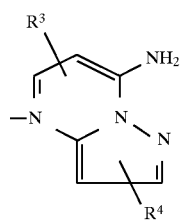

wherein $R^3$ is hydrogen, a lower alkyl, carboxyl or a protected carboxyl group, $R^4$ is hydrogen or a lower alkyl, or with its salt to obtain either the compound of formula (I):

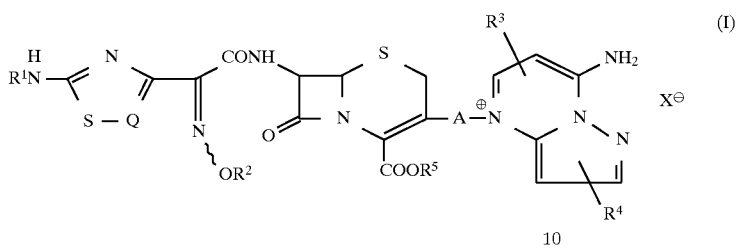

wherein $R^1, R^2, R^3, R^4, R^5, A, Q, X$ and $Y$ and the wavy line have the same meanings as defined above, or its salt.

If necessary and desired, the protecting group may be removed from a cephalosporin derivative of formula (I) thus obtained with an acid and/or by reduction.

Y in formula (VII) is a leaving group which is, for example, a halogen such as chlorine, bromine or iodine, or acetoxy, carbamoyloxy, trifluoromethanesulfonyloxy or p-toluenesulfonyloxy group or the like, preferably bromine, iodine or acetoxy.

Preparation B

A compound of formula (IX):

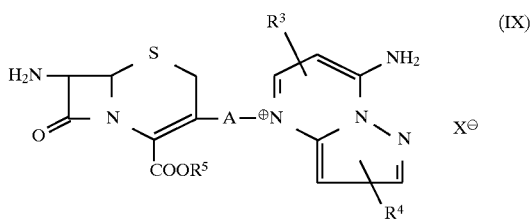

wherein $R^3$ is hydrogen, a lower alkyl, carboxyl or a protected carboxyl group; $R^4$ is hydrogen or a lower alkyl; $R^5$ is hydrogen, an anion or a carboxyl-protecting group; A is methylene or propenylene; X is an organic or inorganic anion, provided that X is excluded when $R^5$ is an anion, is reacted with either a compound of formula (X):

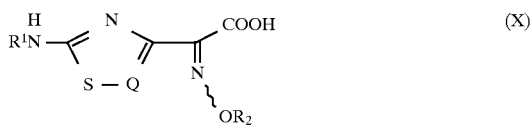

wherein $R^1$ is hydrogen or an amino protecting group; $R^2$ is hydrogen, a lower alkyl or fluoromethyl; Q is nitrogen or CH; the wavy line represents a bond of anti-form or syn-form, or with an appropriate reactive derivative thereof to obtain the compound of formula (I) wherein $R^1, R^2, R^3, R^4, R^5, A, Q$, the wavy line and X have the same meanings as defined above.

If necessary and desired, the protecting group may be removed from a cephalosporin derivative of formula (I) thus obtained with acid and/or by reduction.

The Preparation A and B in the present invention will be described in detail below.

Preparation A

The compounds of formula (I) can be produced by the reaction of a compound of formula (VII) with a compound of formula (VIII) in a solvent such as methylene chloride, chloroform, ether, ethyl acetate, butyl acetate, tetrahdrofuran, acetonitrile, N,N-dimethylformamide, dimethylsulfoxide or a mixture thereof.

And a compound of formula (VIII) can be used as an acid addition salt with an acid such as hydrochloric acid, hydrobromic acid, sulfuric acid, nitric acid, formic acid, acetic acid and the like. In this case the reaction is proceed in the presence of a deacidifying agent such as triethyl amine, diisopropylamine, N,N-dimethylamine, N-methylmorpholine and the like in an amount sufficient to neutralize the acid. If necessary, the compound of formula (VIII) can be used after silanization with a silanizing reagent such as N,O-bis(trimethylsilyl)acetamide and the like.

The reaction is preferably carried out using 1 mol of a compound of formula (VII) and an equivalent amount of 1 to 1.5 mol of a compound of formula (VIII) at a temperature from about –5° C. to about 40° C. for a time in the range of about 30 min to about 10 hr.

The reaction of a compound of formula (VII) wherein Y is acetoxy with a compound of formula (VIII) may be carried out in a solvent such as water, a phosphate buffer, acetone, acetonitrile, methyl alcohol, ethyl alcohol, tetrahydrofuran, dioxane, N,N-dimethyl formamide, dimethylsulfoxide and the like or a mixture thereof. The reaction is preferably carried out in neutral conditions at a reaction temperature ranging from room temperature to 90° C. for between 1 hour and 10 hours. Also the reaction is accelerated when carried out in the presence of an iodine salt such as sodium iodide or potassium iodide, thiocyanate or a quaternary ammonium salt such as trimethylbenzyl- ammonium bromide.

Protection and deprotection of a carboxyl group, an amino group and a hydroxyl group of formula (I) may be carried out by a procedure known and used in β-lactam synthesis.

Typical examples of carboxyl-protecting groups include such groups as tert-butyl, 2,2,2-trichloroethyl, acetoxymethyl, propionyloxymethyl, pivaloyloxymethyl, 1-acetoxyethyl, 1-propionyloxyethyl, 1-(ethoxycarbonyloxy) ethyl, benzyl, 4-methoxybenzyl, 3,4-dimethoxybenzyl, 4-nitrobenzyl, benzhydryl, bis(4-methoxyphenyl)methyl, 5-methyl-2-oxo-1,3-dioxolen-4-yl-methyl, trimethylsilyl, tert-butyldimethylsilyl, and preferably benzhydryl, tert-butyl and 4-methoxybenzyl and the like.

Examples of amino-protecting groups include groups such as trityl, formyl, chloroacetyl, trifluoroacetyl, tert-butoxycarbonyl, trimethylsilyl, tert-butyldimethyl- silyl and the like.

Examples of hydroxyl-protecting groups include groups such as 2-methoxyethoxymethyl, dimethoxymethyl, methylthiomethyl, tetrahydropyranyl, tert-butyl, benzyl, 4-nitrobenzyl, trityl, acetyl, chloroacetyl, 2,2,2-trichloroethoxycarbonyl, benzyloxycarbonyl, trimethylsilyl, tert-butyldimethylsilyl and the like.

The protecting group can be removed by a well known method in the art depending on the type of protecting group. For example, groups such as trityl, formyl, tert-butoxycarbonyl, benzhydryl, tert-butyl, 2-methoxyethoxymethyl, 4-methoxybenzyl may be removed by treating with an inorganic or an organic acid such as hydrochloric acid, formic acid, trifluoroacetic acid, benzenesulfonic acid, p-toluenesulfonic acid, preferably trifluoroacetic acid. Addition of anisole to the reaction mixture when using trifluoroacetic acid as a deprotecting agent results in the improvement of the yield and purity of the product and a decrease in side products.

Also protecting groups such as 4-nitrobenzyloxycarbonyl may be removed by catalytic reduction, and the protecting group such as 2,2,2-trichloroethoxy carbonyl may be removed by reduction with zinc and an acid such as acetic acid, and protecting groups such as chloroacetyl may be removed by treatment with thiourea. And also deprotection of trimethylsilyl group may only be done by water.

The compounds of formula (VII) wherein Y is chlorine may be treated with an iodide such as sodium iodide in a solvent, for example, N,N-dimethylformamide at a temperature from room temperature to that under ice-cooling to give a compound of formula (VII) wherein Y is iodine. The iodide compound is isolated, then used in the next reaction without purification, or if not isolated, is used as such in the next reaction.

Preparation B

The compounds of formula (I) can be produced by reaction of a compound of formula (IX) with a carboxylic acid derivative or an appropriate reactive derivative of the compound of formula (X), for example, an acid halide, a mixed acid anhydride or a reactive ester, in an inert solvent, for example, acetone, dioxane, acetonitrile, tetrahydrofuran, methylenechloride, chloroform, ethylenechloride, benzene, ethyl acetate, N,N-dimethylformamide, dimethylsulfoxide or a mixture thereof.

The reaction is preferably carried out using 1 mol of a compound of formula (IX) and 1 to 1.5 mol equivalent amount of a carboxylic acid or a reactive derivative of formula (X) at a temperature ranging from about −40° C. to about 40° C., preferably, from −10° C. to 10° C.

In the case of using an acid halide as a reactive derivative of the compound of formula (X), the reaction between the compound of the formula (IX) and the compound of formula (X) may preferably be carried out in the presence of a deacidifying agent such as triethylamine, N-methylmorpholine, N,N-dimethylaniline and pyridine. In the preparation of an acid halide, a halogenating agent such as thionyl chloride, phosphorus trichloride, phosphorus tribromide, phosphorus pentachloride, phosphorus oxychloride, oxalyl chloride, phosgene, is used in an amount of 1 to 3 mol relating to 1 mol of the carboxylic acid (X). The reaction is completed within several hours at a temperature in the range of about −20° C. to about 25° C., preferably at from −10° C. to 10° C. Dimethylformamide-phosphorus oxychloride (Vilsmeier reagent) may accelerate the formation of the acid chloride.

In the preparation of a mixed acid anhydride, a chlorocarboxylic ester such as methyl chloroformate, ethyl chloroformate, isobutyl chloroformate may be used in an equivalent amount of 1 to 2 mol relating to 1 mol of a carboxylic acid of formula (X) in the presence of a deacidifying agent such as triethylamine, N-methyl morpholine, N,N-dimethyl aniline, pyridine and the like. The reaction temperature is in the range of about −20° C. to about 20° C. and the reaction time is ranged from 10 min to 60 min.

In the preparation of reactive esters, N-hydroxy derivatives such as N-hydroxysuccinic acid, 1-hydoxybenzotriazol and the like or phenol derivatives such as 4-nitrophenol, 2, 4-dinitrophenol, trichlorophenol and the like may be used in an equivalent amount of 1 to 1.2 mol relating to 1 mol of a carboxylic acid of formula (X) in the presence of a carbodiimide derivative such as N,N-dicyclohexyl-carbodiimide in an equivalent amount of 1 to 1.4 mol relating to 1 mol of the carboxylic acid, and the reaction proceeds at a temperature ranging from −10° C. to 30° C. for 0.5 to 2 hours.

By acylation with a free carboxylic acid of formula (X), a compound of formula (I) can be produced in the presence of a condensing agent, for example, a carbodiimide such as N,N'-dicyclohexylcarbodiimide and the like, or phosphorus oxychloride, N,N-dimethylformamide-phosphorus oxychloride adduct. And a compound of formula (II) can be prepared starting from a compound of formula (I) in accordance with Preparation A.

The starting material of formula (IX) in Preparation B can be produced by the reaction of 7β-acylamino-3-halomethyl-[or 3-(3-halo-1-propenyl)]-3-cephem-4-carboxylate or 7β-acylaminocephalosporanic carboxylate with a compound of formula (VIII) to give a compound of formula (XI):

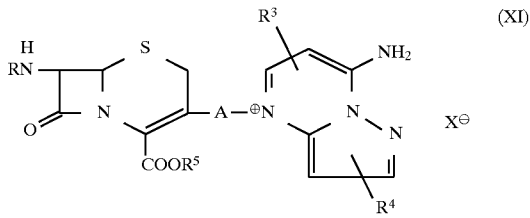

wherein R is an acyl group, $R^3$ is hydrogen, methyl, carboxyl, or a protected carboxyl group, $R^4$ is hydrogen or methyl, $R^5$ is hydrogen, an anion or a carboxyl-protecting group, X is an inorganic or organic anion provided that X is excluded when $R^5$ is an anion, A is methylene or propenylene, followed by deacylation of the 7β-acyl group.

Deacylation can proceed by a conventional technique known in the art, for example, by iminochlorination with phosphorus pentachloride, followed by iminoetheration and hydrolysis with methanol or alternatively by an enzyme of acylase. A phenylacetyl, phenoxyacetyl or aminoadipyl group can be used as an acyl group at the 7β-position.

Also deprotection of a protecting group R in formula (XI) such as formyl, tert-butoxycarbonyl and the like may proceed by treatment with hydrochloric acid or trifluoroacetic acid or the like.

A cephem compound having an aminothiazolyl-fluoromethyloxyiminoacetamido group at the 7β-position has been conventionally produced by introducing the compound of formula (XII):

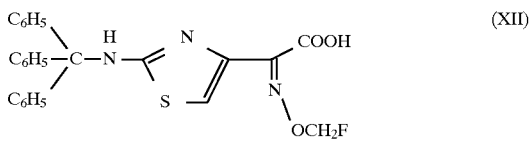

in which the amino group is protected by trityl group, followed by removing the trityl group therefrom.

The compound of the present invention having formula (V):

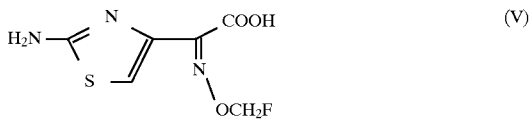

in which the amino group is not protected by a trityl group and is itself a novel compound. According to the present invention, a process for preparation of a cephem compound of formula (III), as referred to in Preparation C, is characterised in that the novel compound (V) is directly reacted with a compound (VI). The compound (V) can be used without protection of the amino group in an aminothiazole group and can be introduced directly into the 7β-amino group of a cephem compound and therefore deprotection of a protecting group is unnecessary. That is a distinct advantage in the preparation of cephem compounds.

The compound (V) can be prepared, for example, by the reaction of hydroxyiminoacetoacetate with fluorobromo methane in the presence of potassium carbonate, then with bromine and thiourea successively to give the methyl 2-(2-aminothiazol-4-yl)-2-fluoromethoxyiminoacetate of formula (XIII):

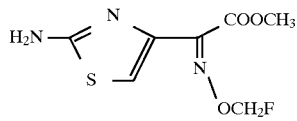

(XIII)

which is hydrolyzed with a base to give the compound (V).

Antimicrobial Activity

Antimicrobial activity in vitro of the compounds of the present invention against the strains described below was determined in accordance with an agar plate dilution method. Each test strain was inoculated into Mueller-Hinton medium Bacto (Difco) in an inoculated bacterial amount (bacterial cell popullation $1 \times 10^6$ CFU/ml) and incubated at 37° C. for 18 hours, followed by determination of the minimum inhibitory concentration (MIC) for the compound of the invention in Examples 1 to 14. Flomoxef (FMOX) and Ceftazidime (CAZ) were used as reference compounds. The results are shown in the Table below.

Test Strains

Bacillus subtilis (ATCC 43223)
Corynebacterium minutissimum (ATCC 23347)
Staphylococcus aureus (ATCC 6538P)
Staphylococcus aureus Methicillin Resistant (ATCC 33591)
Staphylococcus aureus Smith
Streptococcus faecalis (ATCC 10541)
Escherichia Coli (ATCC 10536)
Escherichia Coli (Juhl)
Klebsiella pneumoniae (A 9977)
Proteus vulgaris (A 9539)
Pseudomonas aeruginosa (ATCC 9027)

The ATCC and A numbers are omitted in the table.

| | Antimicrobial Activity Against Standard Strains | | | | | |
|---|---|---|---|---|---|---|
| | Compound in Example Number | | | | | |
| Strain | 1 | 2 | 3 | 4 | 5 | 6 |
| Bacillus subtilis | 0.2 | 0.39 | 0.39 | 1.56 | 0.39 | 1.56 |
| Corynebacterium minutissimum | 0.1 | 0.39 | 0.1 | 0.1 | 0.39 | 0.39 |
| Staphylococcus aureus | 0.2 | 1.56 | 0.1 | 0.39 | 3.13 | 1.56 |
| Staphylococcus aureus (Methicillin Resistant) | 3.13 | 25 | 12.5 | 50 | 12.5 | 25 |
| Staphylococcus aureus Smith | 0.39 | 0.78 | 0.1 | 0.2 | 1.56 | 1.56 |
| Streptococcus faecalis | 3.13 | 25 | 12.5 | 25 | 3.13 | >100 |
| Escherichia Coli | 0.2 | 0.05 | 0.1 | 0.013 | 0.2 | 0.39 |
| Escherichia Coli (Juhl) | 0.1 | 0.05 | 0.1 | 0.013 | 0.1 | 0.78 |
| Klebsiella pneumoniae | 0.1 | 0.025 | 0.1 | 0.003 | 0.1 | 0.39 |
| Proteus vulgaris | 0.2 | 0.025 | 0.05 | 0.003 | 0.2 | 0.78 |
| Pseudomonas aeruginosa | 1.56 | 0.78 | 50 | 6.25 | 0.78 | 50 |
| | Compound in Example Number | | | | | |
| Strain | 7 | 8 | 9 | 10 | 11 | 12 |
| Bacillus subtilis | 0.2 | 0.39 | 3.13 | 0.2 | 1.56 | 0.1 |
| Corynebacterium minutissimum | 0.1 | 0.39 | 0.78 | 0.2 | 0.39 | 0.05 |
| Staphylococcus aureus | 1.56 | 3.13 | 6.25 | 0.78 | 0.78 | 0.78 |
| Staphylococcus aureus (Methicillin Resistant) | 6.25 | 25 | 100 | 1.56 | 6.25 | 1.56 |
| Staphylococcus aureus Smith | 0.78 | 6.25 | 12.5 | 0.78 | 0.2 | 0.39 |
| Streptococcus faecalis | 50 | 6.25 | >100 | 100 | 100 | 3.13 |
| Escherichia Coli | 0.05 | 0.025 | 0.1 | 0.78 | 6.25 | 0.0125 |
| Escherichia Coli (Juhl) | 0.05 | 0.05 | 0.2 | 0.78 | 6.25 | 0.0125 |
| Klebsiella pneumoniae | 0.05 | 0.05 | 0.1 | 0.39 | 6.25 | 0.0125 |
| Proteus vulgaris | 0.025 | 0.0125 | 0.025 | 0.39 | 12.5 | 0.025 |
| Pseudomonas aeruginosa | 1.56 | 12.5 | 100 | 25 | 100 | 0.2 |

Antimicrobial Activity Against Standard Strains -continued

| Strain | Compound in Example Number | | | |
|---|---|---|---|---|
| | 13 | 14 | FMOX | CAZ |
| Bacillus subtilis | 0.1 | 0.2 | 0.39 | 25 |
| Corynebacterium minutissimum | 0.05 | 0.1 | 0.2 | 6.25 |
| Staphylococcus aureus | 0.39 | 0.2 | 0.39 | 25 |
| Staphylococcus aureus Methicillin Resistant | 1.56 | 1.56 | 3.13 | 100 |
| Staphylococcus aureus Smith | 0.2 | 0.2 | 0.39 | 25 |
| Streptococcus faecalis | 6.25 | 25 | 25 | >100 |
| Escherichia Coli | 0.006 | 0.025 | 0.1 | 0.2 |
| Escherichia Coli (Juhl) | 0.0125 | 0.025 | 0.05 | 0.2 |
| Klebsiella pneumoniae | 0.006 | 0.025 | 0.1 | 0.2 |
| Proteus vulgaris | 0.003 | 0.0125 | 0.39 | 0.05 |
| Pseudomonas aeruginosa | 0.39 | 6.25 | >100 | 1.56 |

The compounds of the present invention show a remarkable activity against both sensitive and resistant Gram-positive and Gram-negative bacteria, particularly Gram-negative bacteria, especially Pseudomonas aeruginosa and Methicillin resistant Staphylococcus aureus which are not sensitive to conventional cephem type antibiotics.

The compounds of the present invention of formula (II), the salts or esters thereof can be used for the prophylaxis and therapy of various diseases caused by pathogenic bacteria in human beings and animals.

The antimicrobial composition of the invention comprises at least one of the novel cephem compounds of the present invention as an active ingredient in the form of conventional and pharmaceutically acceptable preparations which are suitable for use in per oral parenteral or external administration, having been incorporated with pharmaceutically acceptable carriers such as an organic or inorganic solid or a liquid filler.

The antimicrobial composition may be in the form of either liquid preparations such as solutions, suspensions, syrups, emulsions, and the like or solid preparations such as tablets, granules, powders, capsules and the like or ointment and the like.

If desired, these preparations may contain auxiliaries, stabilizers, moistening agents, emulsifying agents, absorption-accelerating agents, surface-activating agents and other conventional additives, for example distilled water, Ringer's solution, glucose, sugar syrup, corn-starch, magnesium stearate, talc and the like.

The dosage of novel compounds of the invention depends on the age or sex of the patient, the condition of the disease to be treated and the like, a daily dosage for an adult is in the range of from 0.1 to 5 g and is preferably given in divided doses 1 to 4 times a day. Hereafter the present invention will be described in detail with reference to the following non-limiting examples.

EXAMPLE

Example 1

Preparation of 7β-[2-(2-aminothiazol-4-yl)-2-hydroxyiminoacetamido]-3-(7-aminopyrazolo[1,5-a]pyrimidinium-4-yl)methyl-3-cephem-4-carboxylate(syn-isomer)

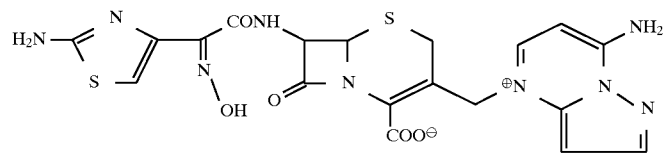

(a) 1.003 g of 4-methoxybenzyl 7β-[2-(2-tritylaminothiazol-4-yl)-2-(trityloxyimino)acetamido]-3-chloromethyl-3-cephem-4-carboxylate (syn isomer) was dissolved in 30 ml of acetone, 442 mg of NaI was added thereto with stirring under ice-cooling, the resulting mixture was stirred at the same temperature for 10 minutes and then at room temperature for 45 minutes followed by removal of the solvent, the residue was extracted with ethyl acetate, the extract was washed with an aqueous sodium chloride solution and dried over $Na_2SO_4$, and then the solvent was distilled off therefrom. The residue thus obtained was dissolved in 12 ml of tetrahydrofuran, 125 mg of 7-aminopyrazolo[1,5-a]-pyrimidine was added thereto with stirring under ice-cooling, the mixture was stirred at the same temperature for 30 minutes and at room temperature for 5 hours and 15 minutes followed by removal of the solvent, the residue was triturated with isopropylether and filtered off. The solid thus obtained was washed with isopropylether and dried to give 1.12 g (92% yield) of 4-methoxybenzyl 7β-[2-(2-tritylaminothiazol-4-yl) -2-trityloxyiminoacetamido]-3-(7-aminopyrazolo[1,5-a] pyrimidinium-4-yl)methyl-3-cephem-4-carboxylate·iodide(syn isomer), which was used in the next reaction without purification.

IRPmax(Nujol)$cm^{-1}$: 3366, 3304, 3165, 1790, 1722, 1663, 1607, 1205, 1219, 1180, 1157, 1099, 1065, 1032, 1003, 966, 918, 903, 827, 754, 702, 662, 635.

NMR δ($CDCl_3$)ppm: 3.50(2 H, br. s), 3.70(3 H,s), 5.06(1 H, d, J=4.5), 5.10(2 H, br. s), 5.19(2 H, s), 5.92(1 H, d. d, J=4.5, 9), 6.40(1 H, s), 6.4–8.1(38 H, m).

(b) 1.05 g of the product obtained in Step (a) was dissolved in 5 ml of methylene chloride, 0.9 ml of anisole and 2 ml of trifluoroacetic acid were successively added dropwise thereto with stirring under ice cooling, the mixture was stirred at the same temperature for 15 minutes and then at room temperature for 2 hours followed by removal of the solvent under reduced pressure, the residue was solidified with isopropylether, and the solid was filtered off, washed with isopropylether and dried to give 550 mg of the trifluoroacetate of the title compound, which was dissolved in MeOH, charged on a polystyrene resin "HP20" column (Mitsubishi Kasei Corp.) and eluted with 20% aqueous methanol. The desired fractions were collected, and concentrated in vacuo to a small volume and lyophilized to give 68 mg (16% yield) of the title compound.

IR υ max(Nujol)cm$^{-1}$: 3319(sh), 3107, 1774, 1666, 1634, 1609, 1549, 1186, 1157, 1109, 1059, 1011, 916, 797, 777, 721.

NMR δ(DMSO-d$_6$)ppm: 3.32, 3.51(2 H, ABq, J=17), 5.10(1 H, d, J=4.5), 5.88(2 H, br. s), 5.77(1 H, d.d, J=4.5, 9), 6.56(1 H, d, J=6.5), 6.75(1 H, s), 6.68(1 H, d, J=2), 8.20(1 H, d, J=6.5), 8.29(1 H, d, J=2), 9.70(1 H, d, J=9).

Example 2

Preparation of 7β-[2-(2-aminothiazol-4-yl)-2-methoxyiminoacetamido]-3-(7-aminopyrazolo[1,5-a]pyrimidinium-4-yl)methyl-3-cephem-4-carboxylate (syn isomer).

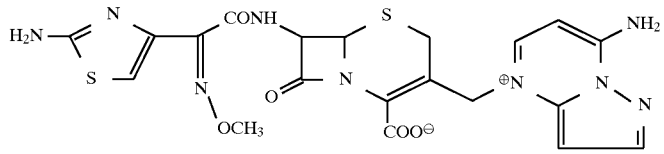

(a) 1038 mg of 4-methoxybenzyl 7β-[2-(2-tritylaminothiazol-4-yl)-2-methoxyiminoacetamido]-3-chloromethyl-3-cephem-4-carboxylate(syn isomer) was dissolved in 30 ml of acetone and 589 mg of NaI was added thereto under ice cooling. The resulting mixture was reacted and treated as described in Example 1, Step (a) to give an iodide, which was reacted with 166 mg of 7-aminopyrazolo[1,5-a]pyrimidine. The resulting mixture was treated as described in Example 1, Step (a) to give 1.18 g (88% yield) of 4-methoxybenzyl 7β-[2-(2-tritylamino-thiazol-4-yl)-2-methoxyiminoacetamido]-3-(7-aminopyrazolo[1,5-a]pyrimidinium-4-yl)methyl-3-cephem-4-carboxylate iodide (syn isomer).

IR υ max(Nujol)cm$^{-1}$: 3273, 1784, 1722, 1665, 1634, 1609, 1250, 1221, 1177, 1124, 1042, 918, 903, 856, 826, 756, 702.

NMR δ(CDCl$_3$+CD$_3$OD)ppm: 3.35(2 H, br. s), 3.74(3 H, s), 3.93(3 H, s), 5.03(1 H, d, J=4.5), 5.10(2 H, br. s), 5.18(2 H, s), 5.77(1 H, d, J=4.5), 6.42(1 H, d, J=6.5), 6.63(1 H, d, J=2), 6.73(2 H, d, J=8.5), 6.9–7.6(17 H, m), 8.02(1 H, d, J=2), 8.21(1 H, d, J=6.5).

(b) Using 1.18 g of the product obtained in Step (a), the reaction was carried out as described in Example 1, Step (b) to give 214 mg (36% yield) of the title compound.

IR υ max(Nujol)cm$^{-1}$: 3325, 3177, 1778, 1666, 1609, 1531, 1186, 1042, 916, 856.

NMR δ(DMSO-d$_6$+CD$_3$OD)ppm: 3.38(2 H, br. s), 3.80(3 H, s), 5.04(1 H, d, J=4.5), 5.18(2 H, br. s), 5.73(1 H, d, J=4.5), 6.41(1 H, d, J=6.5), 6.65(1 H, s), 7.13(1 H, d, J=2), 8.16(1 H, d, J=6.5), 8.21(1 H, d, J=2).

Example 3

Preparation of 7β-2-(2-aminothiazol-4-yl)-2-hydroxyiminoacetamido]-3-[(E)-3-(7-aminopyrazolo[1,5-a]pyrimidinium-4-yl)-1-propenyl]-3-cephem-4-carboxylate (syn isomer).

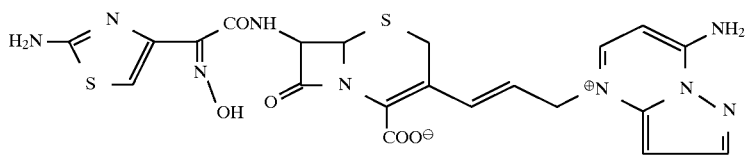

(a) 799mg of 4-methoxybenzyl 7β-[2-(2-tritylaminothiazol-4-yl)-2-trityloxyiminoacetamido]-3-[(Z)-3-chloro-1-propenyl]-3-cephem-4-carboxylate(syn isomer) was dissolved in 25 ml of acetone and 343 mg of NaI was added thereto with stirring under ice cooling, the mixture was stirred at the same temperature for 10 minutes and at room temperature for 1 hour to give an iodide as described in Example 1, Step (a). The obtained iodide was dissolved in a mixture of 6 ml of CH$_3$CN and 5ml of N,N-dimethylformamide, 92 mg of 7-aminopyrazolo[1,5-a]pyrimidine was added thereto and stirred at room temperature for 4.5 hours, followed by distilling off of the solvent under reduced pressure. The residue was solidified by adding isopropylether, and then filtered off and washed with isopropylether and dried in vacuo to give 715 mg (74% yield) of 4-methoxybenzyl 7β-[2-(2-tritylaminothiazol-4-yl)-2-trityloxyimino-acetamido]-3-[(E)-3-(7-aminopyrazolo[1,5-a]pyrimidinium -4-yl)-1-propenyl]-3-cephem-4-carboxylate iodide (syn isomer).

IR υ max(Nujol)cm$^{-1}$: 3325, 1784, 1722, 1666, 1609, 1304, 1248, 1219, 1177, 1157, 1103, 1065, 1034, 1003, 968, 920, 903, 827, 754, 700, 662.

NMR ε(CDCl$_3$+CD$_3$OD)ppm: 3.23, 3.47(2 H, ABq, J=18), 3.81(3 H, s), 4.98(1 H, d, J=4.5), 4.8–5.1(2 H, m), 5.14(2 H, s), 5.84(1 H, d, J=4.5), 6.04(1 H, m), 6.34(1 H, br. d), 6,42(1 H, s), 6.77(2 H, d, J=8.5), 6.7–7.5(35 H, m), 7.87(1 H, br. d), 8.13(1 H, d, J=6).

(b) Using 715 mg of the product obtained in Step (a), a reaction was carried out as described in Example 1, Step (b) to give 57 mg (19% yield) of the title compound.

IR υ max(Nujol)cm$^{-1}$: 3269, 3099, 1771, 1661, 1634, 1609, 1549, 1306, 1254, 1184, 1113, 1059, 1005, 968, 918, 762, 721.

NMR δ(DMSO-d$_6$+CD$_3$OD)ppm: 3.66(2 H, br.s), 5.05(2 H, m), 5.13(1 H, d, J=4.5), 5.65(1 H, d, J=4.5), 6.40(1 H, m), 6.45(1 H, d, J=6.5), 6.67(1 H, d, J=2), 6.78(1 H, s), 6.92(1 H, d, J=13), 8.20(1 H, d, J=2), 8.26(1 H, d, J=6.5).

Example 4

Preparation of 7β-[2-(2-aminothiazol-4-yl)-2-methoxyiminoacetamido]-3-[(E)-3-(7-aminopyrazolo[1,5-a]-pyrimidinium)-1-propenyl]-3-cephem-4-carboxylate (syn isomer).

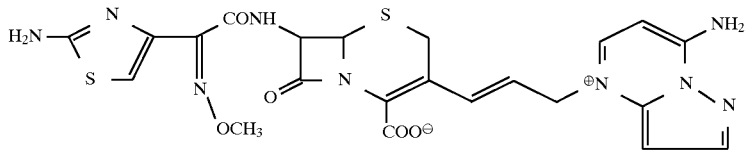

(a) As described in Example 3, Step (a), 900 mg of 4-methoxybenzyl 7β-[2-(2-tritylaminothiazol-4-yl)-2-methoxyiminoacetamido]-3-[(Z)-3-chloro-1-propenyl]-3-cephem-4-carboxylate (syn isomer) was dissolved in 35 ml of acetone and 495 mg of NaI was added thereto with stirring under ice cooling to give an iodide which was reacted with 133 mg of 7-aminopyrazolo[1,5-a]pyrimidine and treated as described in Example 3, Step (a) to give 700 mg (62% yield) of 4-methoxybenzyl 7β-[2-(2-tritylaminothiazol-4-yl)-2-methoxyiminoacetamido]-3-[(E)-3-(7-aminopyrazolo-[1,5-a]pyrimidinium-4-yl)-1-propenyl]-3-cephem-4-carboxylate iodide (syn isomer).

IR τ max(Nujol)cm$^{-1}$: 3271, 1778, 1722, 1661, 1611, 1304, 1248, 1219, 1177, 1159, 1103, 1036, 972, 918, 903, 824, 754, 702.

(b) Using 700 mg of the product obtained in the above step (a), a reaction was carried out as described in Example 1, Step (b) to give 78 mg (21% yield) of the title compound.

IR υ max(Nujol)cm$^{-1}$: 3323, 3271, 3092, 1771, 1663, 1634, 1609, 1306, 1254, 1204, 1184, 1045, 999, 968, 800, 761, 721, 631.

Example 5

Preparation of 7β-[2-(5-aminothiadiazol-3-yl)-2-methoxyiminoacetamido]-3-(7-aminopyrazolo[1,5-a]-pyrimidinium-4-yl)methyl-3-cephem-4-carboxylate (syn isomer).

(a) Using 1.0 g of 4-methoxybenzyl 7β-[2-(5-tritylaminothiadiazol-3-yl)-2-methoxyiminoacetamido]-3-chloro-methyl-3-cephem-4-carboxylate(syn isomer) and 160 mg of 7-aminopyrazolo[1,5-a] pyrimidine, the reaction was carried out as described in Example 1, Step (a) to give 1.147 g (90% yield) of 4-methoxybenzyl 7β-[2-(5-tritylamino-thiadiazol-3-yl)-2-methoxyiminoacetamido]-3-(7-amino-pyrazolo[1,5-a]pyrimidinium-4-yl)methyl-3-cephem-4-carboxylate iodide (syn isomer).

IR υ max(Nujol)cm$^{-1}$: 3273, 3058, 3030, 1784, 1722, 1666, 1634, 1609, 1250, 1221, 1177, 1124, 1042, 756, 702.

NMR δ(CDCl$_3$+CD$_3$OD)ppm: 3.33 (2 H, br. s), 3.67(3 H, s), 3.96(3 H, s), 4.93(1 H, d, J=4.5), 5.07(2 H, br.s), 5.12(2 H, s), 5.76(1 H, d, J=4.5), 6.38(1 H, d, J=6.5), 6.67(1 H, d, J=2), 6.8–7.5(19 H, m), 7.90(1 H, d, J=2), 8.21(1H, d, J=6.5).

(b) 759 mg of the product obtained in Step (a) was dissolved in 5 ml of methylene chloride, and 0.6 mg of anisole and then 1.5 ml of trifluoroacetic acid were successively added dropwise thereto with stirring under ice cooling. The resultant mixture was stirred at the same temperature for 15 minutes and at room temperature for 5 hours followed by distilling off of the solvent, the residue was solidified with isopropylether, filtered off, washed with isopropylether and dried to give 639 mg of trifluoroacetate of the title compound. The trifluoroacetate was dissolved in MeOH, and charged on a polystyrene resin "HP 20" column and eluted with 30% aqueous MeOH. The desired fractions were collected, and concentrated in vacuo to a small volume and lyophilized to give 113 mg (28% yield) of the title compound.

IR υ max(Nujol)cm$^{-1}$: 3323, 3177, 1778, 1666, 1609, 1528, 1307, 1236, 1186, 1153, 1107, 1042, 953, 916, 881, 856, 777, 721.

NMR δ(DMSO-d$_6$)ppm: 3.37(2 H, br. s), 3.82(3H, s), 4.96(1 H, d, J=4.5), 4.99, 5.28(2 H, ABq, J=13), 5.77(1 H, d.d, J=4.5, 9), 6.43(1 H, d, J=6.5), 6.81(1 H, d, J=2), 8.20(1 H, d, J=6.5), 8.17(1 H, d, J=2), 9.65(1 H, s), 10.13(2H, br. s).

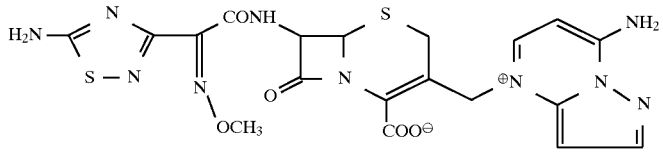

Example 6

Preparation of 7β-[2-(2-aminothiazol-4-yl)-2-hydroxyiminoacetamido]-3-(6-carboxy-7-aminopyrazolo[1,5-a]-pyrimidinium-4-yl)methyl-3-cephem-4-carboxylate (syn isomer).

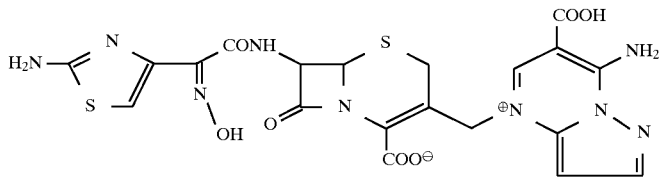

(a) 1.5 g of 4-methoxybenzyl 7β-[2-(2-tritylamino-thiazol-4-yl)-2-trityloxyiminoacetamido]-3-chloromethyl-3-cephem-4-carboxylate(syn isomer) was dissolved in 50 ml of acetone, 661 mg of NaI was added thereto and stirred at room temperature for 1 hour. The reaction mixture was concentrated under reduced pressure. The residue in ethyl acetate was washed with water and dried over Na$_2$SO$_4$ followed by removal of the solvent under reduced pressure. 480 mg of benzhydryl 7-aminopyrazolo[1,5-a]-pyrimidine-6-carboxylate was added to the residue in 1.8 ml of CH$_3$CN and 1.5 ml of N,N-dimethylform-amide. The resultant mixture was stirred at room temperature for 5 hours followed by evaporating off of the solvent. The residue was solidified with isopropylether, filtered off and washed with isopropylether to give 1.82 g (85% yield) of 4-methoxy-benzyl 7β-[2-(2-tritylaminothiazol-4-yl)-2-trityloxy-iminoacetamido]-3-(6-benzhydryloxycarbonyl-7-aminopyrazolo-[1,5-a]pyrimidinium-4-yl)methyl-3-cephem-4-carboxylate iodide (syn isomer).

IR υ max(Nujol)cm$^{-1}$: 3395, 3269, 3231, 3206, 1790, 1693, 1666, 1621, 1614, 1597, 1219, 1175, 1099, 1070, 1032, 968, 750, 700.

NMR δ(CDCl$_3$+CD$_3$OD)ppm: 3.42(2H, br. s), 3.77(3 H, s), 5.03(1 H, d, J=4.5), 5.12(2 H, s), 5.27(2 H, br. s), 5.96(1 H, d, J=4.5), 6.60(1 H, s), 6.72(1 H, d, J=2), 6.80(2 H, d, J=8.5), 6.7–7.6(43 H, m), 8.11(1 H, d, J=2), 9.07(1 H, s).

(b) 1.82 g of the product obtained in Step (a) was dissolved in 6 ml of methylene chloride, and 1.8 ml of anisole and 3.2 ml of trifluoroacetic acid were successively added dropwise with stirring under ice cooling. The reaction mixture was stirred at the same temperature for 10 minutes then at room temperature for 1 hour and concentrated under reduced pressure. The residue in 7 ml of trifluoroacetic acid and 2.2 ml of water was stirred at room temperature for 4 hours and concentrated under reduced pressure. The residue was solidified with isopropylether, filtered off and washed with isopropylether to give 552 mg of the trifluoroacetate of the title compound. The obtained trifluoroacetate in MeOH, was charged on a "HP 20" column and eluted with 20% aqueous MeOH. The fractions containing the desired product were combined, concentrated under the reduced pressure and lyophilized to give 85 mg (12% yield) of the title compound.

IR υ max(Nujol)cm$^{-1}$: 3302, 3204, 3142, 1778, 1705, 1659, 1651, 1645, 1634, 1614, 1308, 1269, 1223, 1190, 1109, 1061, 1013, 920, 791, 721.

NMR δ(DMSO-d$_6$)ppm: 3.33, 3.53(2 H, ABq, J=18), 5.05(1 H, d, J=4.5), 5.32(2 H, br. s), 5.72(1 H, d.d, J=4.5, 9), 6.64(1 H, s), 6.78(1 H, d, J=2), 8.30(1 H, d, J=2), 9.00(1 H, s), 9.63(1 H, d, J=9).

Example 7

Preparation of 7β-[2-(2-aminothiazol-4-yl)-2-methoxyiminoacetamido]-3-(2-methyl-7-aminopyrazolo[1,5-a] pyrimidinium-4-yl)methyl-3-cephem-4-carboxylate (syn isomer).

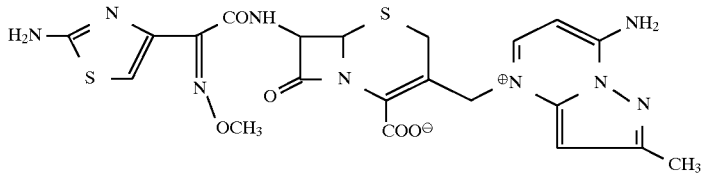

(a) 793 mg of 4-methoxybenzyl 7β-[2-(2-tritylamino-thiazol-4-yl)-2-methoxyiminoacetamido]-3-chloromethyl-3-cephem-4-carboxylate (syn isomer) was reacted with 450 mg of NaI to give an iodide with which 138 mg of 2-methyl-7-aminopyrazolo[1,5-a]pyrimidine was reacted, and treated as described in Example 6, Step (a) to give 900 mg (87% yield) of 4-methoxybenzyl 7β-[2-(2-tritylamino-thiazol-4-yl)-2-methoxyiminoacetamido]-3-(2-methyl-7-amino-pyrazolo[1,5-a]pyrimidinium-4-yl)methyl-3-cephem-4-carboxylate iodide (syn isomer).

IR υ max(Nujol)cm$^{-1}$: 3271, 3175, 1786, 1722, 1661, 1612, 1250, 1221, 1177, 1101, 1036, 901, 826, 812, 754, 702, 662.

NMR δ(CDCl$_3$+CD$_3$OD)ppm: 2.41(3 H, s), 3.37(2 H, br.s), 3.70(3 H, s), 5.02(1 H, d, J=4.5), 5.11(2 H, br.s), 5.13(2 H, s), 5.76(1 H, d, J=4.5), 6.27(1 H, d, J=6.5), 6.32(1 H, s), 6.51(1 H, s), 6.70(2 H, d, J=8.5), 6.9–7.6(17 H, m), 8.22(1 H, d, J=6.5).

(b) 900 mg of the product obtained in Step (a) was reacted as described in Example 6, Step (b) to give 109 mg (23% yield) of the title compound.

IR υ max(Nujol)cm$^{-1}$: 3308(sh), 3267(sh), 1778, 1663, 1612, 1549, 1265, 1223, 1205, 1107, 1043, 972, 953, 920, 856, 800, 768, 733, 721.

NMR δ(DMSO-d$_6$+CD$_3$OD)ppm: 2.45(3 H, s), 3.36, 3.54(2 H, ABq, J=17), 3.91(3 H, s), 5.02(1 H, d, J=4.5), 5.20(2 H, br.s), 5.76(1 H, d, J=4.5), 6.28(1 H, d, J=6.5), 6.30(1 H, s), 6.82(1 H, s), 8.09(1 H, d, J=6.5).

Example 8

Preparation of 7β-[2-(2-aminothiazol-4-yl)-2-methoxyiminoacetamido]-3-(6-carboxy-7-aminopyrazolo [1,5-a]-pyrimidinium-4-yl]methyl-3-cephem-4-carboxylate (syn isomer)

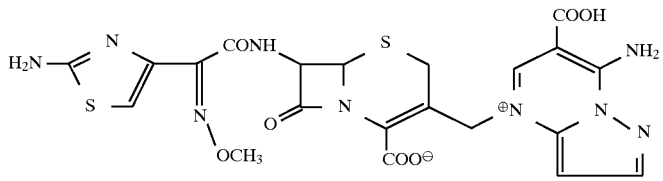

(a) 1.0 g of 4-methoxybenzyl 7β-[2-(2-tritylamino-thiazol-4-yl)-2-methoxyiminoacetamido]-3-chloromethyl-3-cephem-4-carboxylate (syn isomer) was reacted with 567 mg of NaI to give an iodide with which 412 mg of benzhydryl 7-aminopyrazolo[1,5-a]pyrimidine-6-carboxylate was reacted. The reaction was carried out as described in Example 1, Step (a) to give 1.05 g (66% yield) of 4-methoxybenzyl 7β-[2-(2-tritylaminothiazol-4-yl)-2-methoxyiminoacetamido]-3-(6-benzhydryloxycarbonyl-7-aminopyrazolo[1,5-a]-pyrimidinium-4-yl)methyl-3-cephem-4-carboxylate iodide (syn isomer).

IR υ max(Nujol)cm$^{-1}$: 3396, 3271, 1790, 1692, 1666, 1630, 1612, 1597, 1313, 1296, 1277, 1250, 1221, 1177, 1036, 970, 789, 750, 702.

NMR δ(CDCl$_3$)ppm: 3.43(2 H, br. s), 3.73(3 H×2, br. s), 4.78(1 H, d, J=4.5), 5.07(2 H, s), 5.27(2 H, ABq, J=14), 5.83(1 H, d.d, J=4.5, 9), 6.36(1 H, d, J=2), 6.52(1 H, s), 6.81(1 H, s), 6.90(2 H, d, J=8.5), 6.9–7.8(27 H, m), 7.84(1 H, d, J=2), 8.77(1 H, s).

(b) Using 1.0 g of the product obtained in Step (a), a reaction was carried out as described in Example 1, Step (b) to give 91 mg (20% yield) of the title compound.

IR υ max(Nujol)cm$^{-1}$: 3292, 3176, 3132, 1780, 1699, 1634, 1614, 1045, 920, 789, 721.

NMR δ(DMSO-d$_6$)ppm: 3.49(2 H, br. s), 3.83(3 H, s), 5.08(1 H, d, J=4.5), 5.34(2 H, br. s), 5.80(1 H, d.d, J=4.5, 9), 6.77(1 H, s), 6.83(1 H, d, J=2), 8.34(1 H, d, J=2), 9.04(1 H, s).

Example 9

Preparation of 7β-[2-(2-aminothiazol-4-yl)-2-methoxyiminoacetamido]-3-(2-methyl-6-carboxy-7-aminopyrazolo[1,5-a]pyrimidinium-4-yl]methyl-3-cephem-4-carboxylate (syn isomer).

(a) 793 mg of 4-methoxybenzyl 7β-[2-(2-aminothiazol-4-yl)-2-methoxyiminoacetamido]-3-chloromethyl-3-cephem-4-carboxylate was reacted with 450 mg of NaI to give an iodide as described in Example 1, Step (b) and the iodide was reacted with 332 mg of benzhydryl 2-methyl-7-amino-pyrazolo[1,5-a]pyrimidine-6-carboxylate. The reaction was carried out according to the same procedure as that in Example 1, Step (a) to give 980 mg (78% yield) of 4-methoxybenzyl 7β-[2-(2-aminothiazol-4-yl)-2-methoxyiminoacetamido]-3-(2-methyl-6-benzhydryloxycarbonyl-7-aminopyrazolo[1,5-a]pyrimidinium-4-yl)methyl-3-cephem-4-carboxylate iodide (syn isomer).

IR υ max(Nujol)cm$^{-1}$: 3395, 3260, 1790, 1715, 1682, 1663, 1624, 1601, 1339, 1313, 1294, 1269, 1177, 1065, 1036, 704.

NMR δ(CDCl$_3$+CD$_3$OD)ppm: 2.46(3 H, s), 3.32(2 H, br.s), 3.78(3 H, s), 3,83(3 H, s), 4.93(1 H, d, J=4.5), 5.05(2 H, s), 5.16(2 H, br.s), 5.83(1 H, d, J=4.5), 6.14(1 H, s), 6.67(1 H, s), 6.73(1 H, s), 6.9–7.7(29 H, m), 8.62(1 H, s).

(b) Using 980 mg of the product obtained in Step (a), a reaction was carried out as described in Example 1, Step (b) to give 130 mg (22% yield) of the title compound.

IR υ max(Nujol)cm$^{-1}$: 3308, 3200, 1775, 1661, 1614, 1340, 1242, 1182, 1041, 974, 891, 799, 723, 667.

Example 10

Preparation of 7β-[2-(2-aminothiazol-4-yl)-2-hydroxyiminoacetamido]-3-(5-methyl-7-aminopyrazolo[1,5-a]-pyrimidinium-4-yl)methyl-3-cephem-4-carboxylate (syn isomer).

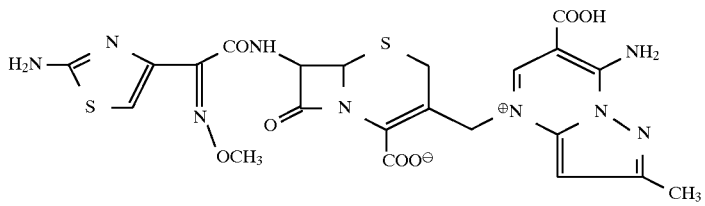

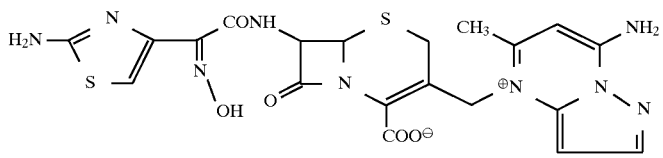

(a) 550 mg of NaI was added to an ice-cooled solution of 1.25 g of 4-methoxybenzyl 7β-[2-(2-tritylamino-thiazol-4-yl)-2-trityloxyiminoacetamido]-3-chloromethyl-3-cephem-4-carboxylate (syn isomer) in 30 ml of acetone was added and the resultant mixture was stirred at room temperature for 3 hours. After evaporating off the solvent, the residue was dissolved in ethyl acetate, the resultant solution was washed with water, dried over $Na_2SO_4$ and concentrated under reduced pressure. The residue was dissolved again in a mixture of 1.5 ml of $CH_3CN$ and 1.0 ml of N,N-dimethylformamide and 172 mg of 5-methyl-7-amino-pyrazolo[1,5-a] pyrimidine was added to it, and the mixture was stirred at room temperature for 24 hours, and then isopropyl ether was added thereto. The resulting precipitate was filtered off and washed with isopropylether to give 435 mg (28% yield) of 4-methoxybenzyl 7β-[2-(2-tritylaminothiazol-4-yl)-2-trityloxyiminoacetamido]-3-(5-methyl-7-aminopyrazolo[1,5-a]pyrimidinium-4-yl)-methyl-3-cephem-4-carboxylate iodide (syn isomer).

IR υ max(Nujol)cm$^{-1}$: 3308, 3200, 1789, 1728, 1666.

(b) Using 430 mg of the product obtained in Step (a), the reaction was carried out as described in Example 1, Step (b) to give 14 mg (8% yield) of the title compound.

IR υ max(Nujol)cm$^{-1}$: 3271, 3100, 1771, 1651, 1593, 1317, 1186, 1107, 1053, 1011, 920, 760, 721.

Example 11

Preparation of 7β-[2-(5-aminothiadiazol-3-yl)-2-hydroxyiminoacetamido]-3-(7-aminopyrazolo[1,5-a]-pyrimidinium-4-yl]methyl-3-cephem-4-carboxylate (syn isomer).

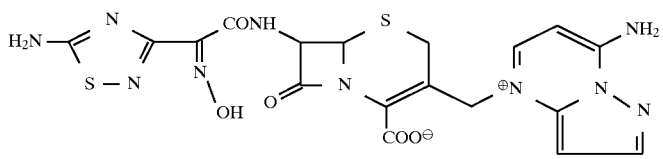

(a) 555 mg of 4-methoxybenzyl 7β-[2-(5-formyl-aminothiadiazol-3-yl)-2-fluoromethoxyiminoacetamido]-3-chloromethyl-3-cephem-4-carboxylate (syn isomer) [IR υ max(Nujol)cm$^{-1}$: 3269, 1782, 1722, 1690, 1634, 1248, 1175, 1105, 1069, 1011, 862, 827. NMR δ($CDCl_3$+$CD_3OD$)ppm: 3.55(2 H, br. s), 3.76(3 H, s), 4.42(2 H, s), 5.03(1 H, d, J=4.5), 5.16(2 H, s), 5.73(2 H, d, J=53), 5.87(1 H, d, J=4.5), 6.80(2 H, d, J-8.5), 7.27(2 H, d, J=8.5), 8.42(1 H, s).] was reacted with 417 mg of NaI to give the iodide with which 116 mg of 7-aminopyrazolo[1,5-a] pyrimidine was reacted as described in Example 1, Step (a) to give 693 mg (89% yield) of 4-methoxybenzyl 7β-[2-(5-formylaminothiadiazol-3-yl)-2-fluoromethoxyiminoacetamido]-3-(7-aminopyrazolo[1,5-a]-pyrimidinium-4-yl)methyl-3-cephem-4-carboxylate iodide (syn isomer).

IR υ max(Nujol)cm$^{-1}$: 1786, 1713, 1659, 1634, 1612, 1250, 1178, 1103, 1069, 1028, 999, 860, 827, 604.

NMR δ(DMSO-$d_6$+$CD_3OD$)ppm: 3.73(3 H, s), 4.9–5.4(5 H, m), 5.72(2 H, d, J=54), 5.86(1 H, d, J=4.5), 6.44(1 H, d, J=6), 6.57(1 H, d, J=2), 6.82(2 H, d, J=8.5), 7.68(2 H, d, J=8.5), 8.17(1 H, d, J=2), 8.22(1 H, d, J=6), 8.40(1 H, s).

(b) 0.5 ml of anisole and 1.5 ml of trifluoroacetic acid were added to an ice-cooled solution of 637 mg of the product obtained in Step (a) in 2 ml of methylene chloride and the resulting solution was stirred for 10 minutes under ice-cooling then at room temperature for 50 minutes. After removing the solvent under reduced pressure, the residue was solidified with isopropylether, and the resulting solid was filtered off, washed with isopropylether, and dissolved in 1.4 ml of MeOH and 1.5 ml of conc. HCl was added dropwise under ice-cooling. The resulting solution was stirred at the same temperature for 15 minutes and at room temperature for 2 hours. After removing the solvent, the residue was added to isopropylether to give a precipitate, which was filtered and purified by "HP 20" column chromatography with 30% aqueous MeOH to give 52 mg (13% yield) of the title compound.

IR υ max(Nujol)cm$^{-1}$: 3347, 1782, 1711, 1664, 1607, 1537.

NMR δ(DMSO-$d_6$+$CD_3OD$)ppm: 3.52(2 H, br.s), 5.12(1 H, d, J=4.5), 5.25(2 H, br.s), 5.67(1 H, d, J=4.5), 6.50(1 H, d, J=6), 6.67(1 H, d, J=2), 8.23(1 H, d, J=2), 8.30(1 H, d, J=6)

Fractions containing 7β-[2-(5-formylamino-thiadiozol-3-yl)-2-fluoromethoxyiminoacetamido]-3-(7-aminopyrazolo-[1,5-a]-pyrimidinium-4-yl)-methyl-3-cephem-4-carboxylate (syn isomer) were eluted next to the title compound and combined and concentrated to give 55 mg (10% yield) of the compound.

IR υ max(Nujol)cm$^{-1}$: 1778, 1659, 1630, 1609, 1531.

NMR δ(DMSO-d6+$CD_3OD$)ppm: 3.45(2 H, br. s), 5.20(1 H, d, J=4.5), 5.27(2 H, br. s), 5.76(2 H, d, J=53), 5.86(1 H, d, J=4.5), 6.35(1 H, d, J=6), 6.70(1 H, d, J=2), 8.20(1 H, d, J=2), 8.30(1 H, d, J=6), 8.68(1 H, s).

Example 12

Preparation of 7β-[2-(5-aminothiadiazol-3-yl)-2-fluoromethoxyiminoacetamido]-3-(7-aminopyrazolo[1,5-a]-pyrimidinium-4-yl]methyl-3-cephem-4-carboxylate (syn isomer).

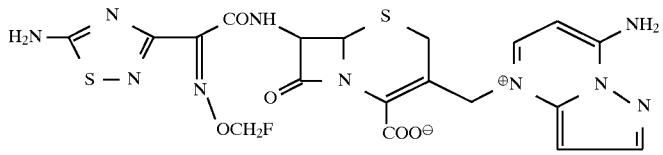

(a) 114 mg of NaI was reacted with 334 mg of 4-methoxybenzyl 7β-[2-(5-aminothiadiazol-3-yl)-2-fluoromethoxyiminoacetamido]-3-chloromethyl-3-cephem-4-carboxylate (syn isomer) [IR υ max(Nujol)cm$^{-1}$: 3418, 3308, 3209, 1778, 1722, 1682, 1614, 1516, 1248, 1175, 1140, 1094, 1063, 1011, 949, 897, 862, 827. NMR δ(CDCl$_3$+CD$_3$OD)ppm: 3.47, 3.65(2 H, ABq, J=18), 3.76(3 H, s), 4.23(2 H, s), 5.03(1 H, d, J=4.5), 5.17(2 H, s), 5.70(2 H, d, J=54.5), 5.80(1 H, d, J=4.5), 6.80(2 H, d, J=8.5), 7.27(2 H, d, J=8.5)] to give the iodide with which 78 mg of 7-aminopyrazolo-[1,5-a]pyrimidine was reacted as described in Example 1, Step (a) to give 435 mg (91% yield) of 4-methoxybenzyl 7β-[2-(5-aminothiadiazol-3-yl)-2-fluoromethoxyimino-acetamido]-3-(7-aminopyrazolo[1,5-a]pyrimidinium-4-yl)-methyl-3-cephem-4-carboxylate iodide (syn isomer).

IR υ max(Nujol)cm$^{-1}$: 3389(sh), 3308, 3260, 3169, 1782, 1720, 1666, 1611, 1514, 1246, 1177, 1063, 997.

NMR δ(DMSO-d$_6$+CD$_3$OD)ppm: 3.51(2 H, br. s), 3.74(3 H, s), 5.11(1 H, d, J=4.5), 6.13(1 H, d, J=6.5), 6.24(1 H, d, J=2), 6.76(2 H, d, J=8.5), 7.24(2 H, d, J=8.5), 8.15(1 H, d, J=2), 8.19(1 H, d, J=6.5).

(b) 658 mg of the product obtained in Step (a) was dissolved in 2 ml of methylene chloride and then 0.5 ml of anisole and 1.0 ml of trifluoroacetic acid were successively added dropwise thereto with stirring under ice-cooling, and the resulting solution was stirred at the same temperature for 30 min then at room temperature for 1 hour. After evaporating off the solvent, the residue was solidified with isopropylether, the resulting solid was filtered off, washed with isopropylether to give 600 mg of the trifluoroacetate of the title compound. The trifluoro-acetate was dissolved in MeOH, charged on a "HP20" column and eluted with 30% aqueous MeOH. The fractions containing the desired product were combined and concentrated under reduced pressure and lyophilized to give 84 mg (19% yield) of the title compound.

IR υ max(Nujol)cm$^{-1}$: 3325, 3173, 1778, 1666, 1609, 1531, 1308, 1236, 1186, 1063, 1001, 951, 916, 872, 862, 797, 779, 735, 721.

NMR δ(DMSO-d$_6$+CD$_3$OD)ppm: 3.42(2 H, br. s), 5.11(1 H, d, J=4.5), 5.26(2 H, br. s), 5.83(1 H, d, J=4.5), 5.69(2 H, d, J=54), 6.48(1 H, d, J=6.5), 6.70(1 H, d, J=2), 8.25(1 H, d, J=2), 8.28(1 H, d, J=6.5).

Example 13

Preparation of 7β-[2-(2-aminothiazol-4-yl)-2-fluoromethoxyiminoacetamido]-3-(7-aminopyrazolo[1,5-a]-pyrimidinium-4-yl]methyl-3-cephem-4-carboxylate (syn isomer).

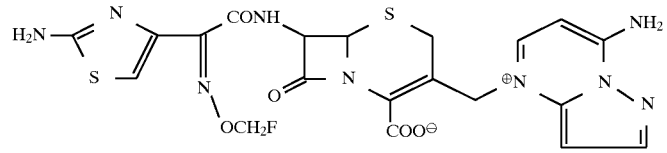

(a) 252 mg of NaI was reacted with 735 mg of 4-methoxybenzyl 7β-[2-(2-aminothiazol-4-yl)-2-fluoromethoxyiminoacetamido]-3-chloromethyl-3-cephem-4-carboxylate (syn isomer) [IR υ max(Nujol)cm$^{-1}$: 3420, 3316, 3207, 3115, 1778, 1722, 1682, 1614, 1304, 1248, 1174, 1163, 1096, 1032, 1018, 989, 826, 735, 696. NMR δ(CDCl$_3$+CD$_3$OD)ppm: 3.50(2 H, br.s), 3.67(3 H, s), 4.38(2 H, s), 4.98(1 H, d, J=4.5), 5.13(2 H, s), 5.76(1 H, d, J=4.5), 5.63(2 H, d, J=54.5), 6.77(1 H, s), 6.76(2H, d, J=8.5), 7.21(2 H, d, J=8.5)] to give the iodide with which 165 mg of 7-aminopyrazolo[1,5-a]-pyrimidine was reacted as described in Example 1, Step (a) to give 770 mg (73% yield) of 4-methoxybenzyl 7β-[2-(2-aminothiazol-4-yl)-2-fluoromethoxyiminoacetamido]-3-(7-aminopyrazolo[1,5-a]-pyrimidinium-4-yl)methyl-3-cephem- 4-carboxylate iodide (syn isomer).

IR υ max(Nujol)cm$^{-1}$: 3321, 3182, 3109, 1781, 1719, 1688, 1614, 1248, 1177, 1150, 1094, 1030, 995.

NMR δ(DMSO-d$_6$+CD$_3$OD)ppm: 3.54(2 H, br. s), 3.70(3 H, s), 4.96(1 H, d, J=4.5), 5.16(2 H, s), 5.20(2 H, br. s), 5.68(2 H, d, J=55), 5.80(1 H, d, J=4,5), 6.30(1 H, d, J=2), 6.37(1 H, d, J=6.5), 6.77(1 H, s), 6.76(2 H, d, J=8.5), 7.21(2 H, d, J=8.5), 8.02(1 H, d, J=2), 8.15(1 H, d, J=6.5).

(b) 770 mg of the product obtained in Step (a) was reacted and treated as described in Example 12, Step (b) to give 88 mg (17% yield) of the title compound.

IR υ max(Nujol)cm$^{-1}$: 3269, 3084, 1778, 1663, 1634, 1609, 1186, 1155, 1078, 1001, 949, 916, 860, 800, 775, 721.

NMR δ(DMSO-d$_6$+CD$_3$OD)ppm: 3.42(2 H, br. s), 5.10(1 H, d, J=4.5), 5.23(2 H, br. s), 5.68(2 H, d, J=54), 5.77(1 H, d, J=4.5), 6.46(1 H, d, J=7), 6.67(1 H, d, J=2), 6.94(1 H, s), 8.18(1 H, d, J=2), 8.24(1 H, d, J=7).

Example 14

Preparation of 7β-[2-(5-aminothiadiazol-3-yl)-2-fluoromethoxyiminoacetamido]-3-[(E)-3-(7- aminopyrazolo-[1,5-a]pyrimidinium-4-yl)-1-propenyl]-3-cephem-4-carboxylate (syn isomer).

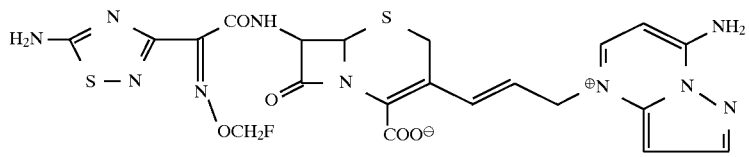

(a) 2.56 g of 4-methoxybenzyl 7β-phenylacetamido-3-[(Z)-3-chloro-1-propenyl]-3-cephem-4-carboxylate [IR υ max(Nujol)cm$^{-1}$: 3265, 1759, 1719, 1661, 1612, 1250, 1221, 1175, 1101, 1036, 824. NMR δ(CDCl$_3$)ppm: 3.20, 3.44(2 H, ABq, J=18), 3.56(2 H, s), 3.71(3 H, s), 3.72(2 H, m), 4.87(1 H, d, J=4.5), 5.03(2 H, s), 5.4–5.9(2 H, m), 6.12(1 H, d, J=11), 6.30(1 H, d, J=9), 6.73(2 H, d, J=8.5), 7.15(5 H, s), 7.17(2 H, d, J=8.5)] was dissolved in 75 ml of dry methylene chloride and the solution was cooled to –40 ° C. 0.68 ml of pyridine and 1.35 g of PCL$_5$ were successively added thereto with stirring. The resulting solution was stirred at room temperature for 2.5 hours and cooled to –40° C. and 46.5 ml of MeOH was dropwise added thereto. The resulting solution was stirred at room temperature for 1.5 hours, and neutralized with an aqueous NaHCO$_3$ solution. The organic layer was washed with brine and water and dried over Na$_2$SO$_4$. After evaporation of the solvent, the residue was purified by silica gel column chromatography (60 g) with a mixture of benzene and ethyl acetate (1/1 volume) to give 1.0 g (51% yield) of 4-methoxybenzyl 7β-amino-3-[(Z)-3-chloro-1-propenyl]-3-cephem-4-carboxylate.

IR υ max(Nujol)cm$^{-1}$: 3400, 3335, 1775, 1728, 1612, 1585, 1516, 1391, 1354, 1302, 1248, 1219, 1175, 1096, 1032, 1003, 826, 785, 735, 696.

NMR δ(CDCl$_3$+CD$_3$OD)ppm: 3.30,3.47(2 H, ABq, J=17), 3.74(3 H, s), 3.83(2 H, m), 4.70(1 H, d, J=4.5), 4.95(1 H, d, J=4.5), 5.08(2 H, s), 5.60(1 H, m), 6.20(1 H, d, J=11), 6.77(2 H, d, J=8.5), 7.21(2 H, d, J=8.5).

(b) 439 mg of 2-(5-aminothiadiazol-3-yl)-2-fluoromethoxyiminoacetic acid (syn isomer) were added to a solution of 650 mg of the product obtained in Step (a) in 10 ml of methylene chloride, and then 1.1 ml of pyridine and 246 μl of phosphorousoxychloride were successively added dropwise with stirring under ice-cooling. The resulting solution was stirred at the same temperature for 10 minutes then at room temperature for 66 minutes, and then added to ethyl acetate and washed with an aqueous HCl solution, an aqueous NaHCO$_3$ solution and water successively and dried over Na$_2$SO$_4$. After evaporation of the solvent, the residue was purified by a silica gel column chromatography with a mixture of benzene and ethylacetate(1/1 volume). The fractions containing the desired product were combined and concentrated to give 250 mg (25% yield) of 4-methoxybenzyl 7β-[2-(5-amino-thiadiazol-3-yl)-2-fluoromethoxyiminoacetamido]-3-[(Z)-3-chrolo-1-propenyl]-3-cephem-4-carboxylate (syn isomer).

IR υ max(Nujol)cm$^{-1}$: 3405, 3304, 3206, 1771, 1719, 1688, 1612, 1302, 1246, 1221, 1175, 1086, 1007, 858, 826, 735.

NMR δ(CDCl$_3$)ppm: 3.37(2 H, br. s), 3.71(3 H, s), 3.81(2 H, m), 4.8–5.3(4 H, m), 5.58(2 H, d, J=54), 5.3–6.0(2 H, m), 6.16(1 H, d, J=11), 6.78(2 H, d, J=8.5), 6.81(2 H, br.s), 7.16(2 H, d, J=8.5), 8.42(1 H, d, J=9).

(c) 576 mg of the product obtained in Step (b) was dissolved in 17 ml of acetone, 188 mg of NaI was added thereto. The resulting mixture was stirred at room temperature for 2 hours to give the iodide. The obtained iodide was dissolved in 3.5 ml of CH$_3$CN and then 124 mg of 7-aminopyrazolo-[1,5-a]-pyrimidine was added thereto. The resultant mixture was stirred at room temperature for 2 hours. After evaporating the solvent, the residue was solidified with isopropylether, and the solid was filtered off and washed with isopropylether to give 489 mg (59% yield) of 4-methoxybenzyl 7β-[2-(5-aminothiadiazol-3-yl)-2-fluoromethoxyiminoacetamido]-3-[(E)-3-(7-aminopyrazolo[1,5-a]pyrimidinium-4-yl)-1-propenyl]-3-cephem-4-carboxylate (syn isomer).

IR υ max(Nujol)cm$^{-1}$: 3317, 1778, 1715, 1668, 1614, 1564, 1520, 1248, 1227, 1177, 1150, 1105, 1007, 920, 866, 825, 772.

NMR δ(DMSO-d$_6$+CD$_3$OD)ppm: 3.68(2 H, br. s), 3.70(3 H, s), 4.9–5.5(5 H, m), 5.67(1 H, d, J=54), 5.78(1 H, d, J=4.5), 6.06(1 H, d, J=5.5), 6.19(1 H, m), 6.27(1 H, d, J=2), 6.74(1 H, d, J=14), 6.80(2 H, d, J=8.5), 7.23(2 H, d, J=8.5), 7.92(1 H,d, J=2), 7.95(1 H, d, J=5.5).

(d) 627 mg of the product obtained in Step (c) was reacted and treated as described in Example 12, Step (b) to give 32 mg (8% yield) of the title compound.

IR υ max(Nujol)cm$^{-1}$: 3300, 3175, 1771, 1666, 1611, 1531, 1306, 1184, 1061, 999, 918, 874, 721.

NMR δ(DMSO-d$_6$+CD$_3$OD)ppm: 3.65(2 H, br. s), 5.01(1 H, d, J=4.5), 5.13(2 H, m), 5.57(2 H, d, J=54), 5.82(1 H, d, J=4.5), 6.30(1 H, m), 6.44(1 H, d, J=6.5), 6.70(1 H, d, J=2), 6.94(1 H, d, J=14), 8.24(1 H, d, J=2), 8.28(1 H, d, J=6.5).

Example 15

Preparation of 7β-[2-(2-aminothiazol-4-yl)-2-fluoromethoxyiminoacetamido]-3-[(E)-3-(7-aminopyrazolo-[1,5-a]pyrimidinium-4-yl)-1-propenyl]-3-cephem-4-carboxylate (syn isomer).

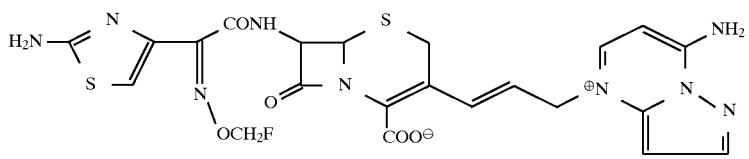

(a) The reaction was conducted in the same manner as described in Example 14, Step (b) except that 2-(2-aminothiazol-4-yl)-2-fluoro-methoxyimino-acetic acid was employed instead of 2-(5-aminothiadiazol-3-yl)-2-fluoro-methoxyiminoacetic acid, and thus 4-methoxybenzyl 7β-[2-(2-aminothiazol-4-yl)-2-fluoromethoxyiminoacetiamido]-3-[(Z)-3-chloro-1 -propenyl]-3-cephem-4-carboxyl-ate (syn isomer) was obtained.

IR υ max(CHCL$_3$)cm$^{-1}$: 3485, 3398, 3320, 3207, 1782, 1724, 1688, 1612, 1250, 1175, 1094, 1034, 1009.

NMR δ(CDCl$_3$)ppm: 3.36(2 H, br. s), 3.72(3 H, s), 3.80(2 H, m), 5.01(1 H, d, J=4.5), 5.04(2 H, s), 5.05(1 H, m), 5.62(2 H, d, J=54), 5.3–6.3(3 H, m), 6.15(1 H, d, J=11), 6.71(2 H, d, J=8.5), 6.73(1 H, s), 7.17(2 H, d, J=8.5), 7.91(1 H, d, J=9).

(b) The product as obtained above was treated in the same manner as described in Example 14, Step (c) to give 4-methoxybenzyl 7β-[2-(2-aminothiazol-4-yl)-2-fluoro-methoxyiminoacetamido]-3-[(E)-3-(7-aminopyrazolo[1,5-a]-pyrimidinium-4-yl)-1-propenyl]-3-cephem-4-carboxylate (syn isomer).

IR υ max(Nujol)cm$^{-1}$: 3314, 3184, 1774, 1715, 1661, 1635, 1611, 1246, 1177, 1150, 1092, 997.

(c) The product as obtained above was treated in the same manner as described in Example 14, Step (d) to give the title compound.

IR υ max(Nujol)cm$^{-1}$: 3371, 3164, 1770, 1669, 1600.

Example 16

Alternative Preparation of 7β-[2-(5-aminothiadiazol-3-yl)-2-fluoromethoxyiminoacetamido]-3-(7-aminopyrazolo-[1,5-a]pyrimidinium-4-yl)methyl-3-cephem-4-carboxylate (syn isomer).

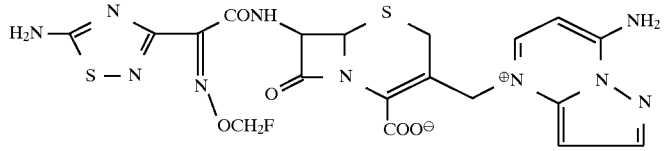

(a) 791 mg of 7β-formylamino-3-chloromethyl-3-cephem-4-carboxylate was dissolved in 250 mg of acetone and 900mg of NaI was added thereto with stirring under ice-cooling. The resultant solution was stirred at the same temperature for 10 minutes and at room temperature for 2 hours, and then diluted with ethyl acetate, washed with water and dried over Na$_2$SO$_4$. After evaporating off the solvent, the residue was dissolved in a mixture of 1.3 ml of dimethylformamide and 1.5 ml of CH$_3$CN, and then 213 mg of 7-aminopyrazolo[1,5-a]pyrimidine was added to the resulting solution, under ice-cooling and stirred at the same temperature for 10 minutes and at room temperature for 4 hours. After evaporating off the solvent, the residue was solidified with isopropylether, and the solid was filtered off and washed with isopropylether to give 1.1 g of 4-methoxybenzyl 7β-formylamino-3-(7-aminopyrazolo-[1,5-a]pyrimidinium-4-yl)methyl-3-cephem-4-carboxy late iodide (syn isomer).

(b) 1.0 ml of anisole and 3 ml of trifluoroacetic acid were added to a solution of 880 mg of the product obtained in the Step (a) in 3 ml of methylene chloride under ice cooling and the mixture was stirred at the same temperature for 10 minutes and at room temperature for 2 hours 40 minutes and concentrated under reduced pressure to remove the solvent. Diisopropylether was added to the residue, and a precipitate formed was filtered off and washed with diisopropylether to give 687 mg (64% yield) of 7β-amino-3-(7-aminopyrazolo-[1,5-a]pyrimidinium-4-yl)-methyl-3-cephem-4-carboxylate trifluoroacetate.

IR υ max(Nujol)cm$^{-1}$: 3148, 1790, 1666, 1609, 1200, 1186, 1140, 1026, 916, 799, 721.

NMR δ(DMSO-d$_6$+CD$_3$OD)ppm: 3.70(2 H, br. s), 5.00(1 H, d, J=4.5), 5.20(1 H, d, J=4.5), 5.32(2 H, br. s), 6.36(1 H, d, J=6.5), 6.53(1 H, d, J=2), 8.15(1 H, d, J=2), 8.18(1 H, d, J=6.5).

(c) 889 μl of N,O-bistrimethylsilylacetamide and 2-(5-aminothiadiazol-3-yl)-2-syn-fluoromethoxyiminoacetyl chloride HCl salt were added to a solution of 650 mg of the product obtained in the Step (b) in 6 ml of methylene chloride, with stirring under ice-cooling. The mixture was stirred at the same temperature for 10 minutes and at room temperature for 2 hours and concentrated under reduced pressure to remove the solvent. The residue was dissolved in 40 ml of methylethylketone, 5 ml of a 10% aqueous HCl solution was added thereto under ice-cooling, stirred for 20 minutes and concentrated under reduced pressure to removed the solvent. The residue was purified by "HP20" column chromatography with a 30% aqueous MeOH solution to give 54 mg (9% yield) of the title compound.

Example 17

Preparation of 2-(2-aminothiazol-4-yl)-2-fluoro-methoxyiminoacetic acid (syn isomer).

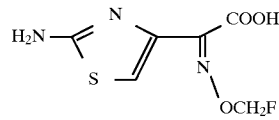

(a) 14.2 g of potassium carbonate was added to a solution of 14.5 g of methyl 2-hydroxyimino-acetoacetate in 50 ml of dimethylsulfoxide, and then 11.6 g of fluoro-bromomethane in 9 ml of N,N-dimethylformamide was added dropwise thereto. The mixture was stirred for 1 hour 30 minutes at room temperature, then poured into ice-water, and the resultant mixture was extracted twice with ethyl acetate. The organic layer was washed with saturated saline, dried over Na$_2$SO$_4$ and concentrated under reduced pressure to remove the solvent. The residue was purified by silica gel column chromatography (120 g) with a mixture solvent of ethyl acetate and toluene (¼ volume) as a eluent to give 4.7 g (27% yield) of methyl 2-fluoromethoxyiminoaceto-acetate (syn isomer).

IR υ max(film)cm$^{-1}$: 1753, 1705, 1620, 1437, 1367, 1313, 1248, 1094, 1051, 1009, 970, 941, 905, 845, 737.

NMR δ(CDCl$_3$)ppm: 2.41(3 H, s), 3.85(3 H, s), 5.65(2 H, d, J=53.5)

(b) 1.36 ml of Br$_2$ in 4 ml of CHCL$_3$ was added dropwise to a solution of 4.6 g of methyl 2-fluoromethoxyiminoacetoacetate in 16 ml of chloroform. The mixture was stirred at room temperature for 2 hours, washed with an aqueous NaHCO$_3$ solution and then brine, dried over Na$_2$SO$_4$ and concentrated under reduced pressure to remove the solvent to give 6 g of crude methyl 2-fluoromethoxy-imino-4-bromoacetoacetate. 7 g of potassium acetate and then 3.56 g of thiourea were added to a solution of the obtained bromoacetoacetate in 29ml of tetrahydorfuran, 20 ml of water. The resulting mixture was stirred at room temperature for 18 hours. The organic layer was separated, and the aqueous layer was extracted with ethyl acetate. The organic layers were combined and washed with an aqueous NaHCO$_3$ solution and brine, dried over Na$_2$SO$_4$, and concentrated under reduced pressure to remove the solvent. The residue was solidified with isopropylether, and the solid was filtered off and washed with isopropylether and dried in vacuo to give 3.2 g (53% yield) of methyl-2-(2-aminothiazol-4-yl)-2-fluoromethoxy-iminoacetate (syn isomer).

IR υ max(Nujol)cm$^{-1}$: 3449, 3256, 3138, 1736, 1614, 1539, 1271, 1086, 1038, 995, 924, 845, 754, 725, 704.

NMR δ(DMSO-d$_6$)ppm: 3.83(3 H, s), 5.67(2 H, d, J=55), 6.98(1 H, s), 7.18(2 H, br. s).

(c) 309 mg of NaOH in 32 ml of water was added dropwise to a solution of 1.5 g of methyl 2-(2-amino-thiazol-4-yl)-2-fluoromethoxyiminoacetoacetate (syn isomer) in 32 ml of MeOH, at 70° C. The mixture was stirred for 2 hours and cooled, and the PH was adjusted to 2 with a 10% aqueous HCl solution followed by extraction with ethyl acetate. The extract was dried over Na$_2$SO$_4$ and concentrated under reduced pressure. The residue was solidified with EtOH and isopropylether, the solid was filtered off and dried in vacuo to give 0.6 g (24% yield) of 2-(2-amino-thiazol-4-yl)-2-fluoromethoxy-iminoacetic acid.

IR υ max(Nujol)cm$^{-1}$: 3304, 3192, 1624, 1537, 1204, 1153, 1099, 1042, 976, 934, 856, 816, 731.

NMR δ(DMSO-d$_6$)ppm: 5.57(2 H, d, J=56), 6.68(1 H, s), 7.04(2 H, br. s).

EXAMPLE OF MEDICINAL PREPARATION

Injection

One thousand mg of 7β-[2-(2-aminothiadiazol-4-yl)-2-fluoromethoxyiminoacetamido]-3-(7-aminopyrazolo[1,5-a]-pyrimidinium-4-yl)methyl-3-cephem-4-carboxylate, 250 mg of sodium chloride and 60 mg of inositol were mixed and dissolved in 20 ml of distilled water. The pH of the resulting solution was adjusted to 4.5 with a 10% aqueous HCl solution, and divided into 5 vials in equal portions after sterile filtration through a membrane filter, and lyophilized. The vials were capped. The thus obtained freeze-dried drug can be used for an injection after dissolving in the appropriate quantity of distilled water and setting into an injection syringe.

What is claimed is:

1. A compound of formula (I):

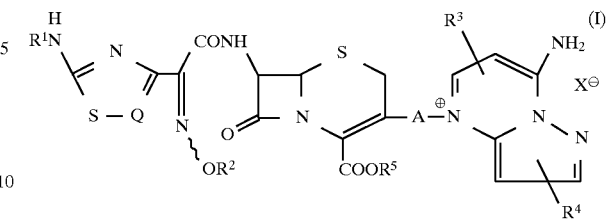

wherein R$^1$ is hydrogen or an amino protecting group; R$^2$ is hydrogen, a lower alkyl or fluoromethyl; R$^3$ is hydrogen, a lower alkyl, carboxyl or a protected carboxyl group; R$^4$ is hydrogen or a lower alkyl; R$^5$ is hydrogen, an anion or a carboxyl-protecting group; A is methylene or propenylene; X is an organic or inorganic anion, provided that X is excluded when R$^5$ is an anion; Q is nitrogen or CH, and the wavy line represents a bond of anti-form or syn-form, or a pharmaceutically acceptable salt thereof.

2. The compound according to claim 1, wherein R$^1$ is hydrogen; R$^2$ is hydrogen, methyl or fluoromethyl; R$^3$ is hydrogen, methyl or carboxyl; R$^4$ is hydrogen or methyl, and the wavy line represents a bond of syn-form.

3. The compound according to claim 1, which is 7β-[2-(5-aminothiadiazol-3-yl)-2-fluoromethoxyiminoacetamido]-3-(7-aminopyrazolo[1,5-a]pyrimidinium-4-yl)-3-cephem-4-carboxylate.

4. The compound according to claim 1, which is 7β-[2-(2-aminothiazol-4-yl)-2-fluoromethoxyimino-acetamido]-3-(7-aminopyrazolo[1,5-a]pyrimidinium-4-yl)-3-cephem-4-carboxylate.

5. The compound according to claim 1, which is 7β-[2-(2-aminothiazol-4-yl)-2-methoxyiminoacetamido]-3-(7-aminopyrazolo[1,5-a]pyrimidinium-4-yl)-3-cephem-4-carboxylate.

6. An antimicrobial composition which comprises as an active ingredient at least one of the compounds of formula (II):

wherein R$^2$ is hydrogen, methyl or fluoromethyl; R$^3$ is hydrogen, methyl or carboxyl; R$^4$ is hydrogen or methyl; A is methylene or propenylene; Q is nitrogen or CH, and the wavy line represents a bond of syn-form, or a pharmaceutically acceptable salt thereof, with an inert carrier or diluent.

* * * * *